US005175402A

United States Patent [19]

Olson

[11] Patent Number: 5,175,402

[45] Date of Patent: Dec. 29, 1992

[54] MERCURY FLOAT SWITCH

[76] Inventor: Delwyn L. Olson, 3915 101st W., Bradenton, Fla. 34210

[21] Appl. No.: 866,402

[22] Filed: Apr. 10, 1992

[51] Int. Cl.[5] .......... A01H 35/18

[52] U.S. Cl. .......... 200/84 R; 73/322.5; 200/230; 417/40

[58] Field of Search .......... 174/101.5, 151; 73/308, 73/313, 317, 322.5; 307/118; 340/623, 625; 361/427, 428; 417/40, 297.5; 200/61.2, 61.45 R, 61.52, 81.9 HG, 190, 230, 84 R, 84 A, 84 B

[56] References Cited

U.S. PATENT DOCUMENTS

| | | | |
|---|---|---|---|
| 3,621,168 | 11/1971 | Durand | 200/84 B |
| 4,021,144 | 5/1977 | Matsusaka | 417/40 |
| 4,086,457 | 4/1978 | Niedermeyer | 200/84 R |
| 4,223,190 | 9/1980 | Olson | 200/84 R |
| 4,778,957 | 10/1988 | Crowell | 200/84 R |

*Primary Examiner*—Gerald P. Tolin

[57] ABSTRACT

An improved housing for a mercury float switch as disclosed in U.S. Pat. No. 4,223,190. The improved housing includes an exterior bracket connected to a side wall of the housing structured to releasably yet securely retain lead electrical wires extending from the mounting shaft of the float switch whereby the exposed lead electrical wires may be arcuately configured, then wedgedly locked between the bracket and side wall. By this arrangement, free pivotal movement of the float switch within the housing is maintained while holding the exposed lead electrical wires above the bilge water level, as in a boat bilge.

3 Claims, 2 Drawing Sheets

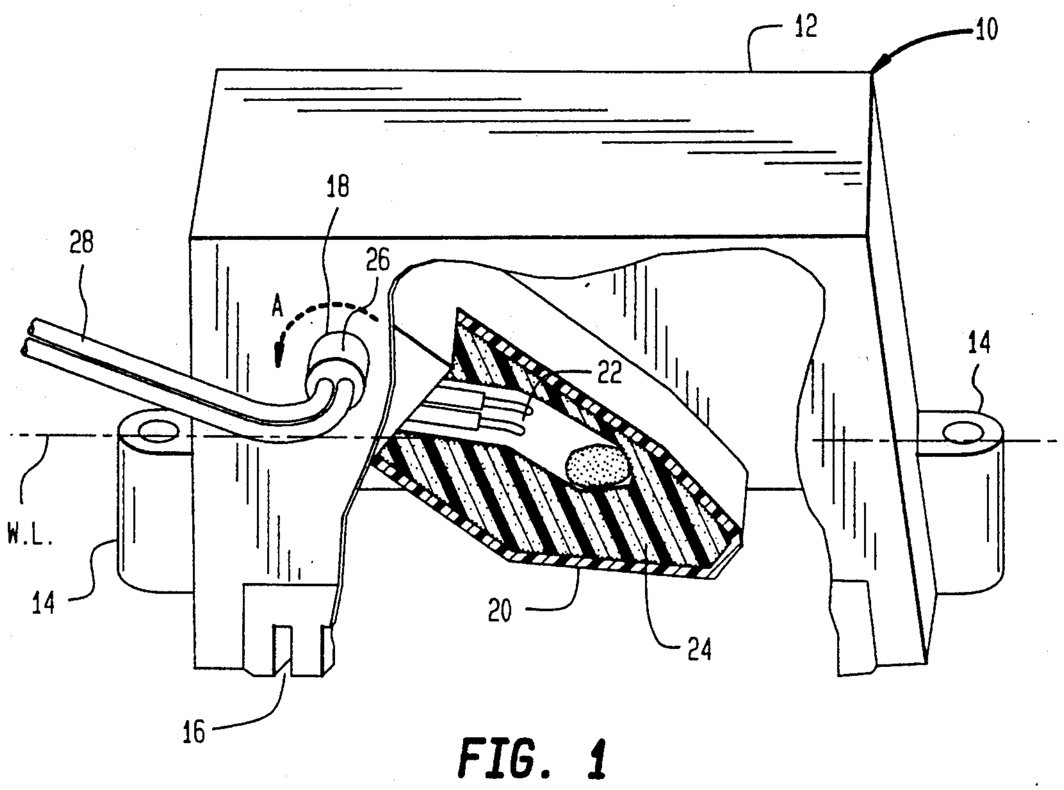
FIG. 1
(PRIOR ART)
FIG. 2
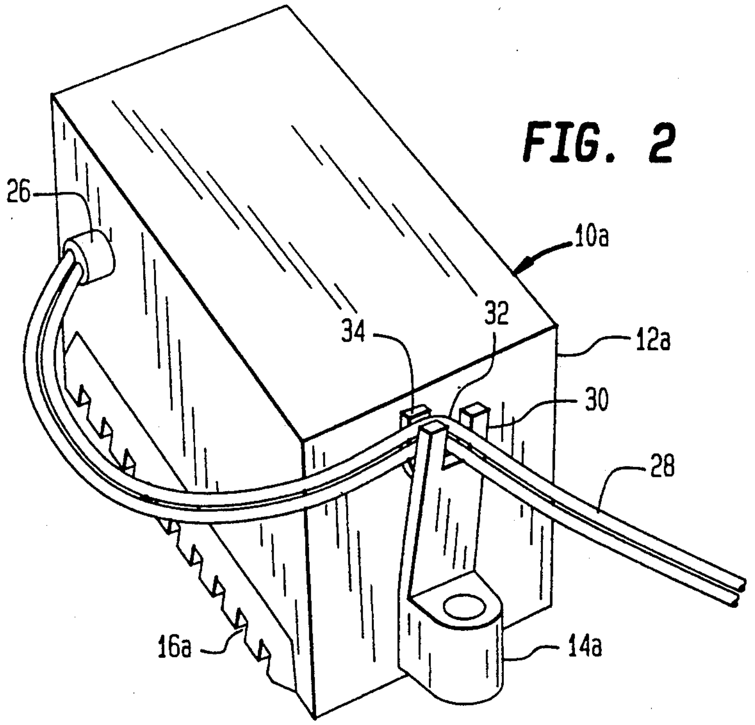

MERCURY FLOAT SWITCH

BACKGROUND OF THE INVENTION

This invention relates generally to float-type electrical switches, and more particularly to an improvement in a mercury float switch for use in the operation of bilge or sump pumps or the like.

Reference is made to my previous patent, U.S. Pat. No. 4,223,190 which discloses and claims a mercury float switch having a float operable by variations in the water level in the bilge of a boat to control the operation of a bilge pump or the like. That device includes a mercury activated float switch pivotally supported within a mounting bracket, the bracket itself then supportable or connectable to the bilge bottom surface.

Applicant has also invented an unpatented improvement to the '190 invention as shown in FIG. 1 of the drawings contained herein. This unpatented improvement is directed to an integrally molded housing having upright side walls and a top panel, the side walls defining an opening at the bottom thereof into which water within the bilge may freely flow. This unpatented improvement serves to more fully protect the pivotal action of, and the mercury float switch from encountering debris and objects in a boat bilge. Note that the lead electrical wires in both the '190 patent and the unpatented improvement extend in exposed fashion from one end of the mounting shaft of the mercury float switch.

By either of the above arrangements, the exposed lead electrical wires will either fall into bilge water, deteriorating the electrical wire coating and then wire itself or must be drawn upwardly taught and fastened to another structure of the boat by conventional clips and fastening means. When being installed in this fastion, the exposed lead electrical wires are likely to be either drawn too taut so as to inhibit free pivotal movement of the mercury float switch contained within the housing or be allowed to hang so loosely as to partially sit within bilge water.

The present invention overcomes this limitation by providing a bracket connected to the exterior of the housing so that a proper arcuate positioning of the exposed lead electrical wires may be established for free mercury float switch movement, while maintaining this portion of the lead electrical wiring out of bilge water. Thereafter, the remaining exposed electrical wire may be redirected and extended upwardly away from the float switch to be fastened to other structure of the boat.

BRIEF SUMMARY OF THE INVENTION

This invention is directed to an improved housing for a mercury float switch as disclosed in U.S. Pat. No. 4,223,190. The improved housing includes an exterior bracket connected to a side wall of the housing structured to releasably yet securely retain lead electrical wires extending from the mounting shaft of the float switch whereby the exposed lead electrical wires may be arcuately configured, then wedgedly locked between the bracket and side wall. By this arrangement, free pivotal movement of the float switch within the housing is maintained while holding the exposed lead electrical wires above the bilge water level, as in a boat bilge.

It is therefore an object of this invention to provide an improved float switch for controlling the operation of a bilge or sump pump or the like which eliminates the likelihood of the exposed lead electrical wiring coming in contact with contaminated bilge or sump water.

It is yet another object of this invention to provide an improved mercury float switch having a housing which affords accurate positioning of the exposed electrical lead wiring in a fixed position as they extend from the housing so as to avoid any bending upon the free pivotal movement of the float switch.

It is yet another object of this invention to provide an easily adjustable means for proper arcuate positioning and securing of the lead electrical wiring extending from the mounting shaft of the float switch pivotally mounted within the housing.

In accordance with these and other objects which will become apparent hereinafter, the instant invention will now be described with reference to the accompanying drawings.

BRIEF DESCRIPTION OF THE DRAWINGS

FIG. 1 is a perspective partially broken view of a prior art device.

FIG. 2 is a perspective view of the present invention.

DETAILED DESCRIPTION OF THE INVENTION

Figure 3:
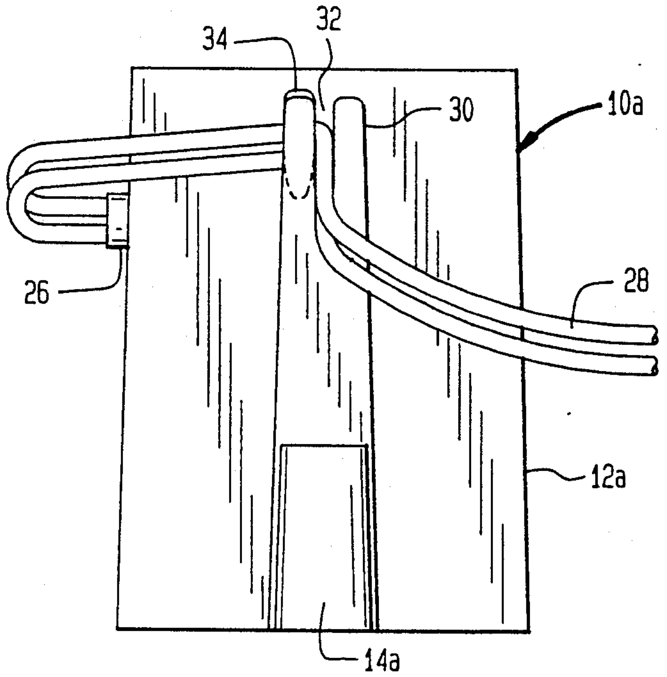
FIG. 3 is an end elevation view of FIG. 2.

Referring now to the drawings, and particularly to FIG. 1, the prior art device is there shown at numeral 10. This prior art device 10 includes a molded plastic thin wall housing 12 having downwardly extending side walls and a top panel. The side walls downwardly extend to be supported on a horizontal surface such as the bilge of a boat and to define an opening into which bilge water may flow. Slots 16 along opposing side walls facilitate water flow into the housing 12, while preventing debris from entering therethrough. Mounting lugs 14 are also provided to secure the housing 12 to the bottom surface of the bilge.

A mercury float switch 20 pivotally connected to a transverse mounting shaft 26 is positioned within housing 12. The float switch 12 is filled with a rigid foam material 24 having a mercury filled tube 22 embedded there within. Electrical contacts (not shown) are positioned at one end of the glass mercury tube 22 and in electrical contact with the ends of lead electrical wires 28 such that, when the float switch 20 is pivoted on support shaft 26 in the direction of arrow A by the raising of the water level WL, a globule of mercury within the mercury tube 22 moves to complete the circuit between the lead electrical wires 28.

Figure 4:
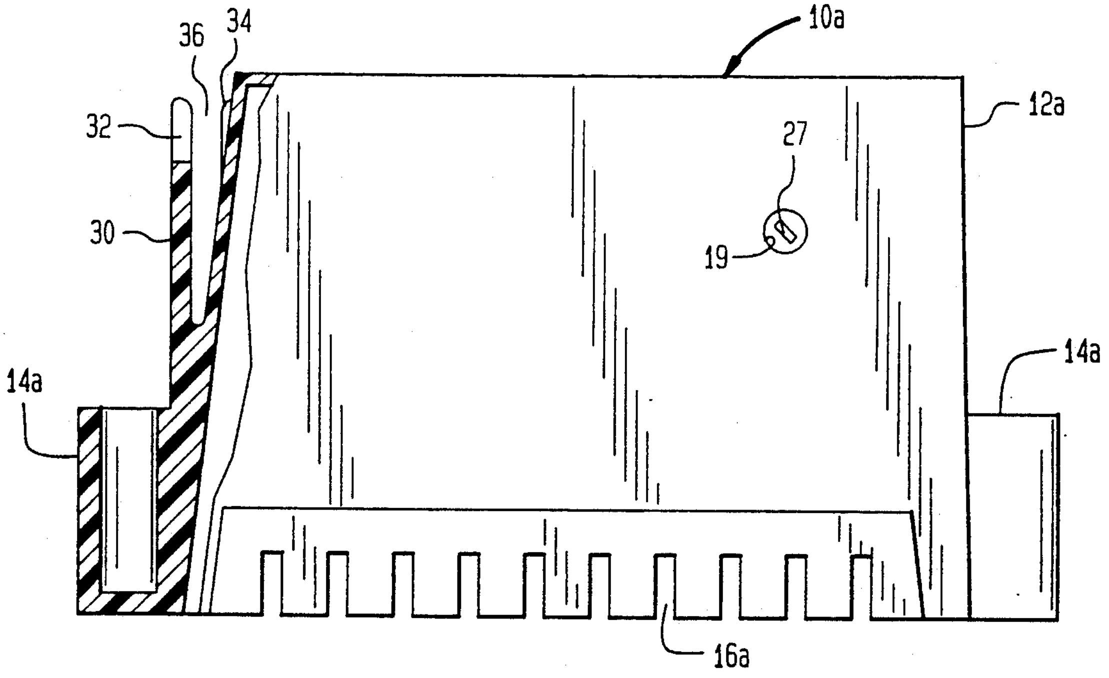
FIG. 4 is a side elevation partially broken view of FIG. 2.

Referring additionally to FIGS. 2, 3 and 4, the invention is shown generally at numeral **10*a* and includes the same mercury float switch 20 (not shown) pivotally supported on mounting shaft 26 and its extension which outwardly extend through apertures 18 and 19, respectively, formed in alignment one to another within the corresponding side walls of housing 12*a***.

As disclosed in the '190 patent, the lead electrical wires extend in either direction from a hollow support shaft. In the improved prior art device disclosed in FIG. 1, both lead electrical wires 28 extend in one direction from support shaft 26.

To accomplish the objects of the present invention, an integrally molded upright, cantilevered bracket 30 is provided integrally molded to the corresponding upright side wall as shown. This bracket 30 is spaced from the corresponding side wall of housing 12*a* so as to form a slot 36 therebetween. This slot 36 is of a size such that the lead electrical wires 28 will snugly and wedgedly fit therebetween and yet be releasable therefrom for further adjustment.

As best seen in FIGS. 2 and 3, a proper arcuate positioning and length selection of the exposed portion of lead electrical wires 28 between support shaft 26 and bracket 30 is easily selected so as to maintain this portion of the lead electrical wires in a generally horizontal orientation while avoiding putting any binding pressure upon the smooth, free pivotal action of support shaft 26 and its extension 27.

To further enhance the lockable wedging action of the lead electrical wires 28 between bracket 30 and the housing 12*a*, an elongated upright bead 34 is also provided. This bead focuses the locking pressure against the electrical lead wires 28 so as to further prevent movement of the lead electrical wires 28 at that point.

A yet further locking enhancer of the lead electrical wires 28 is in the form of an upright notch 32 formed downwardly into the distal end of bracket 30. By this arrangement, the lead electrical wires 28 are forced to bend through about ninety degrees after exiting from between bead 34 and the opposing surface of bracket 30, thus making it virtually impossible to inadvertently pull the electrical lead wires sufficiently so as to alter the arcuate adjustment selected for the electrical lead wire between mounting bracket 26 and bracket 30.

This notch 32 also serves to redirect the lead electrical wires 28 away from housing 12*a* in a manner more suitable for support attachment to the part of the boat or sump upwardly therefrom.

This housing 12*a* also includes mounting lugs 14*a* and water slots 16*a* as previously described with respect to FIG. 1.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. In a mercury float switch including a float body formed of a light, corrosion-resisting foam materal, a housing disposed in supporting engagement over said float body, a mercury tube having a globule of mercury contained therein, said mercury tube potted on the interior of said foam material, a pair of switch contacts mounted on the interior of said mercury tube, a mounting shaft, attached to said float body and so disposed to have its opposite ends extend outwardly therefrom, said mounting shaft having lead electrical wires disposed therewithin, said lead electrical wires connected at one end to said contacts and extending outwardly from one end of said mounting shaft, said mounting shaft pivotally mounted within said housing and fixedly connected in supporting relation to said float body, said mounting shaft and said float body rotatable about a longitudinal axis of said mounting shaft, said globule of mercury disposed to bridge said contacts and electrically interconnect said lead electrical wires upon predetermined pivotal movement of said float body, the improvement comprising:

a bracket connected to an outer surface of an upright side wall of said housing, said bracket spaced apart from and generally parallel to said side wall;

said bracket and said side wall defining a slot receiving said lead electrical wires therewithin whereby a portion of said lead electrical wires extending between said mounting shaft and said slot may be arcuately shaped and held above a high water level whereupon said float body is rotated about said mounting shaft axis so that said mercury globule just contacts said pair of switch contacts.

2. A mercury float switch as set forth in claim 1, further comprising:

a notch formed in said bracket extending from a free distal end thereof;

said notch wedgedly receiving said lead electrical wires therewithin and redirecting said lead electrical wires from said slot.

3. A mercury float switch as set forth in claim 2, further comprising:

a bead formed in said side wall positioned opposingly to said bracket whereby said slot is narrowed between said bead and said bracket to increase releasable wedging pressure against said lead electrical wires.

* * * * *